United States Patent [19]

Golik et al.

[11] Patent Number: 5,902,822
[45] Date of Patent: May 11, 1999

[54] 7-METHYLTHIOOXOMETHYL AND 7-METHYLTHIODIOXOMETHYL PACLITAXELS

[75] Inventors: Jerzy Golik, Southington; Dolatrai M. Vyas, Madison, both of Conn.

[73] Assignee: Bristol-Myers Squibb Company, Princeton, N.J.

[21] Appl. No.: 09/025,270

[22] Filed: Feb. 18, 1998

Related U.S. Application Data

[XX .
[60] Provisional application No. 60/039,480, Feb. 28, 1997.
[51] Int. Cl.$^6$ ........................ A61K 31/335; C07D 305/14
[52] U.S. Cl. ........................... 514/449; 549/510; 549/511
[58] Field of Search ........................ 514/449; 549/510, 549/511

[56] References Cited

U.S. PATENT DOCUMENTS

| | | | |
|---|---|---|---|
| 4,814,470 | 3/1989 | Colin et al. | 514/449 |
| 4,960,790 | 10/1990 | Stella et al. | 514/449 |
| 5,254,580 | 10/1993 | Chen et al. | 514/449 |
| 5,272,171 | 12/1993 | Ueda et al. | 514/449 |
| 5,294,637 | 3/1994 | Chen et al. | 514/449 |
| 5,352,806 | 10/1994 | Gunawardana et al. | 549/510 |

FOREIGN PATENT DOCUMENTS

| | | |
|---|---|---|
| 590267A2 | 4/1994 | European Pat. Off. . |
| 600517A1 | 6/1994 | European Pat. Off. . |
| 0604910A1 | 7/1994 | European Pat. Off. . |
| 617034A1 | 9/1994 | European Pat. Off. . |
| 0694539A1 | 1/1996 | European Pat. Off. . |
| 764643A1 | 3/1997 | European Pat. Off. . |
| WO93/06093 | 4/1993 | WIPO . |
| WO94/08984 | 4/1994 | WIPO . |
| WO94/14787 | 7/1994 | WIPO . |
| WO94/20485 | 9/1994 | WIPO . |
| WO96/00724 | 1/1996 | WIPO . |
| WO96/03394 | 2/1996 | WIPO . |

OTHER PUBLICATIONS

E. K. Rowinsky and R. C. Donehower, "The Clinical Pharmacology and Use of Antimicrotubule Agents in Cancer Chemotherapeutics," Pharmac. Ther., 52: 35–84, 1991.
C. M. Spencer and D. Faulds, "Paclitaxel, A Review of its Pharmacodynamic and Pharacokinetic Properties and Therapeutics Potential in the Treatment of Cancer," Drugs, 48(5), 794–847, 1994.
K.C. Nicolaou, et al, "Chemistry and Biology of Taxol," Angew. Chem., Int. Ed. Engl., 33: 15–44, 1994.
Greene and Wuts, Protective Groups In Organic Synthesis, 2nd Ed., John Wiley & Sons, and McOmie, 1991.
Protective Groups In Organic Chemistry, Ed.J.F.W. McOmie, Plenum Press, 1973.
S.–H. Chen, et al, "First Syntheses of Novel Paclitaxel (Taxol) Analogs Modified at the C4–Position," J. Org. Chem., 59, pp. 6156–6158, 1994.

S.–H. Chen et al, "Structure–Activity Relationships of Taxol: Synthesis and Biological Evaluation of C2 Taxol Analogs," Bioorganic and Medicinal Chemistry Letters, vol. 4, No. 3, pp. 479–482, 1992.
R.A. Johnson, "Taxol Chemistry. 7–O–Triflates as Precursors to Olefins and Cyclopropanes," Tetrahedron Letters, vol. 35, No. 43, pp. 7893–7896, 1994.
X. Liang and G.I. Kingston, "Synthesis and Biological Evaluation of Paclitaxel Analogs Modified in Ring C," Tetrahedron Letters, vol. 36, No. 17, pp. 2901–2904, 1995.
G. Roth, et al, "Reaction of Paclitaxel and 10–Desacetyl Baccatin III with Diethylamino Sulfurtrifluoride," Tetrahedron Letters, vol. 36, No. 10, pp. 1609–1612, 1995.
S.–H. Chen, et al, "The Chemistry of Taxanes: Reaction of Taxol and Baccatin Derivatives with Lewis Acids in Aprotic and Protic Media," Tetrahedron, vol. 49, No. 14, pp. 2805–2828, 1993.
L.L. Klein, "Synthesis of 9–Dihydrotaxol: A Novel bioactive Taxane," Tetrahedron Letters, vol. 34, No. 13, pp. 2047–2050, 1993.
Physician's Desk Reference, 49th Edition, Medical Economics, p. 682, 1995.
J. Kant, et al, "A Chemoselective Approach to Functionalize the C–10 Position of 10–Deacetylbaccatin III. Synthesis and Biological Properties of Novel C–10 Taxel Analogues," Tetrahedron Letters, 35, No. 31, pp. 5543–5546, 1994.
S.G. Arbuck, et al, Taxol® Science and Applications, edited by M. Suffness, 1995 (CRC Press Inc., Boca Raton, Florida), pp. 379–415.
K. C. Nicolaou, et al, "Chemical Synthesis and Biological Evaluation of C–2 Taxoids," J. Am. Chem. Soc., 117, pp. 2409–2420, 1995.
K. V. Rao, et al, "Synthesis and Evaluation of Some 10–Mono–and 2',10–Diesters of 10–Deacetylpaclitaxel," J. Med. Chem., 38, pp. 3411–3414, 1995.
G. I. Georg, et al, "Steroeselective Synthesis 9β–Hydroxytaxanes Via Reduction With Samarium Diiodide," Tetrahedron Letters, 36(11), pp. 1783–1786, 1995.
F.A. Holmes, et al, Taxane Anticancer Agents Basic Science and Current Status, edited by G.I. Georg, et al, 1995, American Chemical Society, Washington, D.C. 31–57.
W. Rose, "Evaluation of Madison 109 Lung Carcinoma as a Model for Screening Antitumor Drugs," Cancer Treatment Reports, 65, No. 3–4, pp. 299–312, 1981.
J. Golik, et al, "Synthesis and Antitumor Evaluation of Paclitaxel Phosphonoxymethyl Ethers: A Novel Class of Water Soluble Paclitaxel Pro–Drugs," Bioorganic & Medicinal Chemistry Letters, 6(15), pp. 1837–1842, 1996.

*Primary Examiner*—Ba K. Trinh
*Attorney, Agent, or Firm*—Samuel J. DuBoff

[57] ABSTRACT

The present invention concerns novel paclitaxel derivatives, their use as antitumor agents, and pharmaceutical formulations.

11 Claims, No Drawings

7-METHYLTHIOOXOMETHYL AND 7-METHYLTHIODIOXOMETHYL PACLITAXELS

This application claims the priority benefit of provisional application No. 60/039,480 dated Feb. 28, 1997.

BACKGROUND OF THE INVENTION

1. Field of the Invention

The present invention concerns antitumor compounds. More particularly, the invention provides novel paclitaxel derivatives, pharmaceutical formulations thereof, and their use as antitumor agents.

2. Background Art

Taxol® (paclitaxel) is a natural product extracted from the bark of Pacific yew trees, *Taxus brevifolia*. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutics," *Pharmac. Ther.*, 52:35–84, 1991; by Spencer and Faulds in "Paclitaxel, A Review of its Pharmacodynamic and Pharmacokinetic Properties and Therapeutic Potential in the Treatment of Cancer," *Drugs*, 48 (5) 794–847, 1994; by K. C. Nicolaou et al. in "Chemistry and Biology of Taxol," *Angew. Chem., Int. Ed. Engl.*, 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, D.C., 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named Taxotere® (docetaxel) has also been found to have good antitumor activity. The structures of paclitaxel and Taxotere® are shown below along with the conventional numbering system for molecules belonging to the class; such numbering system is also employed in this application.

Taxol®: R=Ph; R'=acetyl
Taxotere®: R=t-butoxy; R'=hydrogen

SUMMARY OF THE INVENTION

This invention describes novel antitumor compounds in which the C-7 hydroxy group of the taxane core is derivatized as either a 7-methylthiooxomethyl ether or a 7-methylthiodioxomethyl ether. This invention relates to novel antitumor compounds represented by formula I, or pharmaceutically acceptable salts thereof

I wherein: R is aryl, substituted aryl, $C_{1-6}$ alkyl, $C_{2-6}$ alkenyl, $C_{3-6}$ cycloalkyl, or heteroaryl;
$R^A$ is hydrogen;
$R^B$ is independently —NHC(O)-aryl, —NHC(O)-substituted aryl, —NHC(O)-heteroaryl, —NHC(O)OCH$_2$Ph, or —NHC(O)O—($C_{1-6}$ alkyl);
$R^C$ is hydrogen;
$R^D$ is hydroxy;
$R^2$ is phenyl or substituted phenyl;
$R^4$ is methyl, ethyl, propyl, cyclopropyl or —O—($C_1$–$C_3$ alkyl);
L is O;
$R^6$ and $R^{6'}$ are hydrogen;
One of $R^{7'}$ and $R^7$ is hydrogen and the other is —OCH$_2$S(O)$_n$CH$_3$;
n=1 or 2;
$R^9$ and $R^{9'}$ are independently hydrogen or hydroxy or $R^9$ and $R^{9'}$ together form an oxo (keto) group;
$R^{10}$ is hydrogen, hydroxy or —OC(O)—($C_1$–$C_6$ alkyl);
$R^{10'}$ is hydrogen;
$R^{14}$ is hydrogen or hydroxy; and
$R^{19}$ is methyl.

A more preferred embodiment are compounds with the structure I or pharmaceutically acceptable salts thereof, having the following groups:

I wherein R is phenyl, p-hydroxyphenyl, p-fluorophenyl, p-chlorophenyl, p-Tolyl, isopropyl, isopropenyl, isobutenyl, isobutyl, cyclopropyl, furyl, or thienyl;
$R^A$ is hydrogen;
$R^B$ is independently —NHC(O)Ph, or —NHC(O)O—($C_{1-6}$ alkyl);
$R^C$ is hydrogen;
$R^D$ is hydroxy;
$R^2$ is phenyl;

$R^4$ is methyl;
L is O;
$R^6$ and $R^{6'}$ are hydrogen;
n=0, 1, or 2;
$R^{7'}$ is hydrogen;
$R^7$ is —OCH$_2$S(O)$_n$CH$_3$;
n=1 or 2;
$R^9$ and $R^{9'}$ together form an oxo (keto) group;
$R^{10}$ is hydroxy or —OC(O)CH$_3$;
$R^{10'}$ is hydrogen;
$R^{14}$ is hydrogen; and
$R^{19}$ is methyl.

An even more preferred embodiment are compounds with the structure I or pharmaceutically acceptable salts thereof, having the following groups:

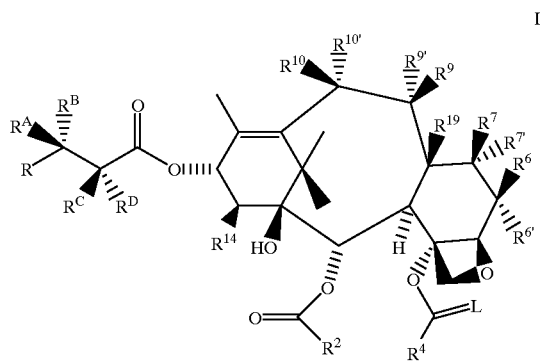

I wherein R is phenyl or p-fluorophenyl;
$R^A$ is hydrogen;
$R^B$ is —NHC(O)Ph;
$R^C$ is hydrogen;
$R^D$ is hydroxy;
$R^2$ is phenyl;
$R^4$ is methyl;
L is O;
$R^{6'}$ and $R^6$ are hydrogen,
$R^{7'0}$ is hydrogen;
$R^7$ is —OCH$_2$S(O)$_n$CH$_3$;
n=1 or 2;
$R^9$ and $R^{9'}$ together form an oxo (keto) group;
$R^{10}$ is —OC(O)CH$_3$;
$R^{10'}$ is hydrogen;
$R^{14}$ is hydrogen;
$R^{19}$ is methyl.

Another aspect of the present invention provides a method for inhibiting tumor in a mammalian host which comprises administering to said mammalian host an antitumor effective amount of a compound of formula I.

Yet, another aspect of the present invention provides a pharmaceutical formulation which comprises an antitumor effective amount of a compound of formula I in combination with one or more pharmaceutically acceptable carriers, excipients, diluents or adjuvants.

DETAILED DESCRIPTION

In the application, unless otherwise specified explicitly or in context, the following definitions apply. The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methylbutane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, cyano, azido, $C_{1-6}$ alkylamino, di-$C_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis*, 2d Ed., 1991, John Wiley & Sons, and McOmie; and *Protective Groups in Organic Chemistry*, 1975, Plenum Press.

"Ph" means phenyl; "ipr" means isopropyl; "DAST" means diethylamino sulfur trifluoride.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

The term "taxane" or "taxane core" refers to moieties with a framework of the structure:

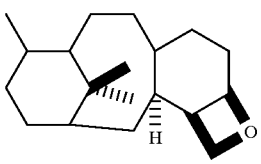

The new products that have the general formula I display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by techniques from the conventional organic chemistry repertoire. Schemes 1 and 2, which depict processes that compounds within the scope of formula I can be made, are only shown for the purpose of illustration and are not to be construed as limiting the processes to make the compounds by any other methods.

The best method for preparing 7-methylthiooxomethyl and 7-methylthiodioxomethyl taxane analogs of claim 1 is by oxidation of the corresponding 7-methylthiomethyl ether analogs. The preparation of the 7-methylthiomethyl ether analogs of taxanes is described in the following three references: by J. Golik et. al. in Biorganic & Medicinal Chemistry Letters 1996, 6(15), pp. 1837–1842; in PCT Application WO 96/00724 published on Jan. 11, 1996; in European Publication 0604910A1 published on Jul. 6, 1994; and in European Publication 0694539A1 published on Jan. 31, 1996.

The sulfoxide derivatives are best prepared via controlled oxidation of the appropriate taxane 7-methylthiomethyl ether analog using a slightly more than a stoichiometric amount of a peracid such as m-chloroperoxybenzoic acid (mCPBA). Other peracids known in the art could be utilized; particularly preferred is sodium periodate (NaIO$_4$). The preferred solvent is dichloromethane and a reduced temperature of −5 degrees C. was utilized. The oxidation reaction of paclitaxel methylthioether 1 to produce a diastereomeric mix of sulfoxides 2 and 3 is shown in Scheme 1. These sulfoxides can be separated by chromatography techniques such as HPLC. The sulfoxide can also be produced in other aprotic solvents such as 1,2-dichloroethane, ethylacetate, or tetrahydrofuran for example. Other temperatures may be utilized but excess of the peracid oxidant at elevated temperatures must be avoided since this favors sulfone formation. Other oxidant systems which typically produce sulfoxides such as sodium periodate or tetrabutylammonium periodate can also be utilized. These reagents would be employed in methyl alcohol, ethyl alcohol, propyl alcohols, butanols, dioxane, tetrahydrofuran, ether, diglyme, or dichloromethane either alone or in combination with a water cosolvent.

The sulfone derivatives can be prepared via oxidation with metachloroperoxybenzoic acid (or other peracids) in stoichiometries greater than two equivalents in aprotic solvents such as methylene chloride, ethylacetate, or tetrahydrofuran for example. Scheme 2 describes the oxidation of paclitaxel methylthiomethylether 1 to the sulfone 4. Alternatively aqueous hydrogen peroxide in sovents such a acetic acid, methanol, ethanol, or other alcohols could be utilized for the oxidation to the sulfone.

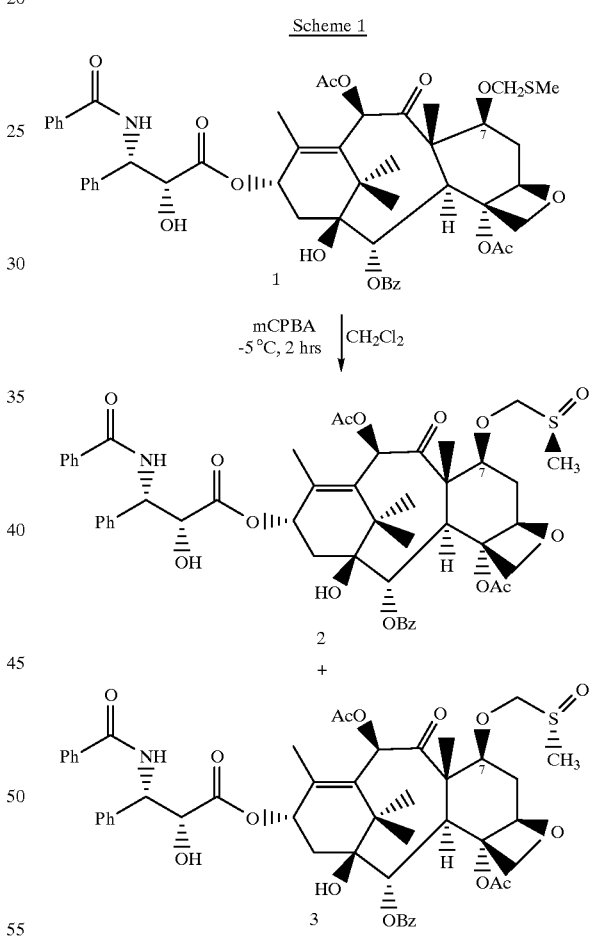

The schemes and examples herein describe compounds containing a paclitaxel sidechain. It is well known in the art that the chemistry that is used for making the 7-methylthiooxomethyl and 7-methylthiodioxomethyl derivatives disclosed herein with a paclitaxel sidechain works with other standard sidechains or on baccatin III analogs which contain a suitably protected C-13 hydroxy group. Examples of suitable C-13 protecting groups include trialkylsilyl, 2,2,2-trichloroethyl carbonate (i.e. TROC), or phenoxy acetate.

Scheme 2

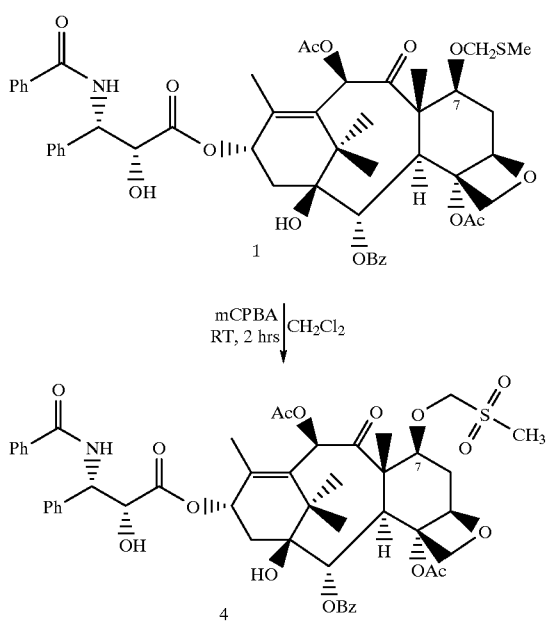

Some of the schemes refer to a hydroxy protecting group, preferably trialkylsilyl group. It is to be understood that hydroxy protecting group may be a carbonate or ester group —C(O)OR$^x$ or —C(O)R$^x$. Thus when such a group is employed as a hydroxy protecting group, it may either be removed to generate the free hydroxy protecting group or it may remain as a part of the final product.

By now there are many publications teaching the introduction of a wide variety of groups onto a taxane core. By using these well established methods or obvious variants thereof, the starting taxanes of formula VII, or hydroxy protected analogues thereof, can be readily made. For example, for transforming C4-acetoxy into other functional groups see, S. H. Chen et al., *J. Organic Chemistry*, 59, pp 6156–6158 (1994) and PCT application WO 94/14787 published Jul. 7, 1994; for converting C2-benzoyloxy to other groups see, S. H. Chen et al, *Bioorganic and Medicinal Chemistry Letters*, Vol. 4, No. 3, pp 479–482 (1994); K. C. Nicolaou et al., *J. Am. Chem. Soc.*, 1995, 117, 2409 and European Patent Application 617,034A1 published Sep. 28, 1994; for modifying C10-acetyloxy see, K. V. Rao et al., *J. Med. Chem.*, 38, pp 3411–3414 (1995), J. Kant et al., *Tetrahedron Letters*, Vol. 35, No. 31, pp 5543–5546 (1994); and U.S. Pat. No. 5,294,637 issued Mar. 15, 1994; for making C10 and/or C7 unsubstituted (deoxy) derivatives see, European Patent Application 590,267A2 published Apr. 6, 1994 and PCT application WO 93/06093 published Apr. 1, 1993; for making C-10 epi hydroxy or acyloxy compounds see PCT application WO 96/03394; for making C-10 deoxy-C-10 alkyl analogs see PCT application WO95/33740; for making 7b,8b-methano, 6a,7a-dihydroxy and 6,7-olefinic groups see, R. A. Johnson, *Tetrahedron Letters*, Vol. 35, No 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and G. I. Kingston, *Tetrahedron Letters*, Vol. 36, No. 17, pp 2901–2904 (1995); for making C7-epi-fluoro see, G. Roth et al, *Tetrahedron Letters*, Vol 36, pp 1609–1612 (1995); for forming C7 esters and carbonates see, U.S. Pat. No. 5,272,171 issued Dec. 21, 1993 and S. H.

Chen et al., *Tetrahedron*, 49, No. 14, pp 2805–2828 (1993); for 9a- and 9b-hydroxy taxanes see, L. L. Klein, *Tetrahedron Letters*, Vol 34, No 13, pp 2047–2050 (1993), PCT application WO 94/08984 published Apr. 28, 1994, U.S. Pat. No. 5,352,806 issued Oct. 4, 1994, PCT application WO 94/20485 published Sep. 15, 1994, and G. I. Georg et. al. *Tetrahedron Letters*, Vol 36, No 11, pp 1783–1786 (1995).

DESCRIPTION OF SPECIFIC EMBODIMENTS

The specific examples that follow illustrate the synthesis of the compounds of the instant invention, and are not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), CDCl$_3$ (deuterochloroform) and other conventional deuterated solvents. The infrared (IR) spectral description include only absorption wave numbers (cm$^{-1}$) having functional group identification value.

Celite is a registered trademark of the Johns-Manville Products Corporation for diatomaceous earth.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); (DHQ)$_2$PHAL (hydroquinine 1,4-phthalazinediyl diether). Tf=triflate=trifluoromethanesulfonate; LRMS (low resolution mass spectrometry); ESI (electrospray ionization).

EXAMPLE 1

Preparation of Mixture of Sulfoxides 2 & 3

A sample of compound 1, 7- methylthiomethyl paclitaxel, 37 mg (1 equiv.) was dissolved in 2 ml of methylene chloride and cooled to −5° C. Solid m-chloroperoxybenzoic acid (80–85%) 7.8 mg (0.9 equiv.) was added. The reaction mixture was stirred at −5° C. for 2 hours. The reaction was quenched with 10 μl of dimethyl sulfide. The solvent was removed and the residue was purified on a preparative silica gel plate 20×20×0.05 cm (EM Merck) using methylene chloride:acetone (2:1, v/v) for elution. The major product was eluted from silica gel with acetone and re-purified by preparative TLC as previously, only this time, chloroform:methanol (10:1, v/v) was used as a solvent system. The final product weighing 27.1 mg, which is 1:1 weight ratio (maximum 10% ratio error) of compounds 2 and 3, was obtained in 72% yield after evaporation of solvents in vacuo.
MS (FAB/NOBA+NaI+KI): m/z 930, [M+H]$^+$; m/z 952, [M+Na]$^+$; m/z 968, [M+K]$^+$
$^1$H-NMR (300 MHz, CDCl$_3$): 1.15 (3H, s), 1.18 (3H, s), 1.70–1.82 (7H), 1.85–1.96 (1H, m), 2.18 (3H, s), 2.27–2.30 (1H), 2.35–2.36 (3H), 2.44 (3H), 2.70–2.88 (1H, m), 3.81–3.87 (2H), 4.12–4.17 (2H), 4.26–4.29 (1H, d), 4.36–4.39 (1H, d), 4.50–4.60 (1H, m), 4.74–4.78 (1H, m), 4.86–4.89 (1H, brd), 5.63–5.66 (1H, m), 5.74–5.78 (1H, dd), 6.13–6.19 (1H, t), 6.36 (1H, s), 7.14–7.17 (1H, dd), 7.34–7.50 (10H), 7.56–5.59 (1H), 7.72–7.76 (2H), 8.07–8.10 (2H).
$^{13}$C-NMR (75 MHz, CHCl$_3$): 10.51, 10.65, 14.69, 20.86, 21.06, 22.61, 26.57, 33.45, 34.27, 35.60, 43.18, 46.69, 55.06, 57.26, 57.48, 72.03, 73.26, 74.38, 74.98, 75.15, 76.45, 78.61, 80.73, 80.94, 81.10, 82.36, 83.68, 85.49, 88.02, 127.06, 127.12, 128.27, 128.65, 128.73, 128.96, 130.17, 131.91, 133.34, 133.77, 138.09, 140.23, 140.33, 166.90, 167.06, 169.39, 169.55, 170.49, 172.61, 201.56.

EXAMPLE 2

Preparation of Sulfone 4

A sample of 7- methylthiomethyl paclitaxel 30 mg was dissolved in 2 ml of methylene chloride and treated with 14.5 mg of m-chloroperoxybenzoic acid (80–85%) at room temperature. After 2 hours the solvent was allowed to evaporate in vacuo to dryness and the residue was purified by chromatography on preparative silica gel plate 20×20× 0.05 cm (EM Merck) using toluene:acetone (2:1, v/v) and re-purified using ethyl acetate:hexane (1:1, v/v). The major product was extracted from silica gel with acetone. Concentration in vacuo provided 28 mg (90% yield) of the product.
MS (FAB/NOBA+NaI+KI): m/z 946, [M+H]$^+$; m/z 968, [M+Na]$^+$; m/z 984, [M+K]$^+$
$^1$H-NMR (300 MHz, CDCl$_3$): 1.15 (3H, s), 1.18 (3H, s), 1.74 (3H, s), 1.80 (3H, d), 1.90–1.99 (1H, m), 2.17 (3H, s), 2.28–2.31 (1H, d), 2.35 (3H, s), 2.77 (3H, s), 2.79–2.87 (1H, m), 3.71 (1H, brs), 3.79–3.81 (1H, d), 4.14–4.29 (4H), 4.67–4.71 (1H,d), 4.76–4.77 (1H, d), 4.88–4.90 (1H, d), 5.64–5.68 (1H, d), 5.74–5.77 (1H, dd), 6.13–6.19 (1H, brt), 6.33 (1H, s), 7.04–7.07 (1H, d), 7.32–7.50 (10H), 7.57–7.59 (1H), 7.71–7.74 (2H), 8.07–8.10 (2H).
$^{13}$C-NMR (75 MHz, CHCl$_3$): 10.58, 14.67, 20.86, 21.09, 22.58, 26.52, 29.25, 33.02, 35.59, 38.03, 43.14, 46.58, 55.06, 57.48, 72.10, 73.20, 74.38, 75.22, 76.44, 78.57, 80.92, 82.94, 83.54, 127.07, 128.34, 128.70, 128.75, 129.01, 130.18, 131.98, 133.21, 133.62, 133.80, 137.98, 140.35, 166.89, 167.13, 169.57, 170.58, 172.61, 201.69.

EXAMPLE 3

Preparation of Mixture of Sulfoxides 2 & 3

To a solution of compound 1 (1.007 g, 1.10 mmol) in 15 mL of methylene chloride at −78° C. was added mCPBA (55%, 344 mg, 1.10 mmol). The solution was held at −78° C. for 2 hours, then warmed to −40° C. for 2 hours and then 0° C. for 18 hours. Another portion of mCPBA was added in 5 mL of methylene chloride at 0° C. (55%, 344 mg, 1.10 mmol) and stirred for 1 hour. The solution was diluted with methylene chloride and washed with NaHCO$_3$ and dried over MgSO$_4$. The solution was concentrated and chromatographed over silica gel using hexane/ethyl acetate (1:1) and then hexane/ethyl acetate/methanol (1:1:0.1) to give 645 mg of sulfone (62% yield), 250 mg of a first mixture of sulfoxides (90% early elute and 8% later elute) (24% yield), and 120 mg of a second mixture of sulfoxides (57% early elute and 42% later elute) (11% yield).

EXAMPLE 4

Alternate Preparation of Sulfoxides 2 & 3

A solution of NaIO$_4$ (516 mg, 2.414 mmol) in 5 mL of water was cooled to 0° C. To this solution was added compound 1 (2.006 g, 2.195 mmol) in 5 mL of methanol. Additional methanol was added to keep the solution homogeneous and stirred for 4 hours. The solution was diluted with ethyl acetate and washed three times with water and once with brine. The organic fraction was dried over MgSO$_4$ and concentrated. The residue was chromatographed over silica gel using hexane/ethyl acetate/methanol (1:1:0.1) to give 1.584 g of a mixture of sulfoxides (57% early elute and 42% later elute) (78% yield).

EXAMPLE 5

Preparation and Separation of Pure Compounds 2 & 3

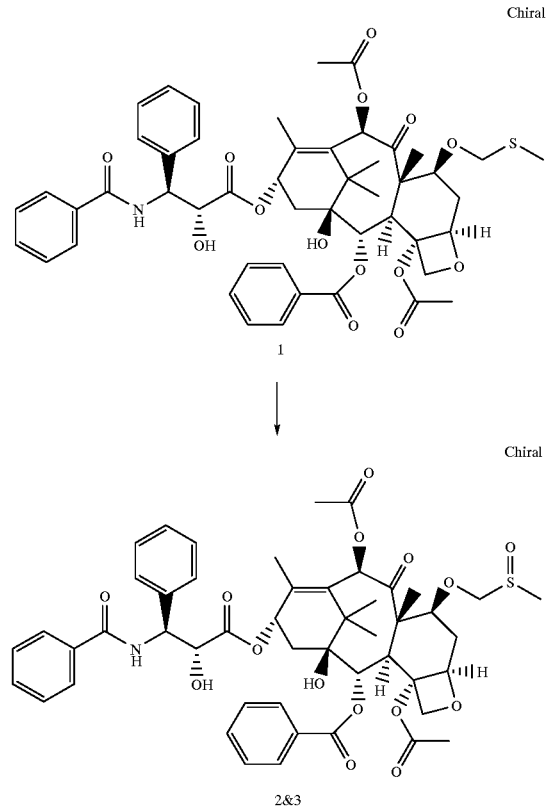

To a 100 ml 2 neck round flask bottle was added Compound 1 (1.0 g, 1.09 mmol) in MeOH (methanol, 60 mL). The solution was cooled to 0° C. To this solution was added a solution of NaIO$_4$ (258 mg, 1.21 mmol) in water (3 mL).

The reaction was stirred for 1 hr and the progress followed by HPLC. HPLC analysis showed only a small amount of sulfoxide being formed. After 8 hr, the reaction was only 7% complete. It was allowed to stir overnight at room temperature. In the morning, an HPLC was obtained. Reaction had proceeded to approximately 40% completion. A white precipitate had formed. It was determined that was $NaIO_4$. The addition of 20 mL water clarified the solution and the reaction was allowed to proceed over the weekend. HPLC showed the reaction to be nearly complete. Water (10 mL) was added to the slurry, and the solution was filtered on a medium frit glass funnel. The solid was washed through the filter with MeOH into a 100 mL round bottom flask, and the solvent was removed by rotavap to give a white solid (1.126 g). It was pumped down under high vacuum to give 856 mg (84% yield) (Chiral mixture 2 & 3).

Separation of Diasteromer Compounds 2 & 3
Semi-prep LC of diasteromers 2 & 3
LC (Liquid-Phase Chromatography) conditions:
solvent A: 90% $H_2O$, 10% MeCN
solvent B: 10% $H_2O$, 90% MeCN
Isocratic: 50% B
Injection volume: 0.5 mL
Concentration: 25 mg/mL
Diluent: 50:50 A+B
Column: YMC-PACK ODS 5-5 um 120A°, 250×20 mm I.D. CAT #AA12S05-2520WT Ser #20444472B(W)
Flow rate: 9.50 mL/min
early eluting diasteromers: RT (retention time)=25.00 to 26.50 minutes later eluting diasteromers: RT=28.10 to 29.4 minutes
all together, 14 injections of mixture 2 & 3 were made. Each collection was concentrated to remove the MeCN. The aqueous white solid was extracted with $CH_2Cl_2$ (3×35 mL), dried over $Na_2SO_4$, filtered and concentrated to give a white solid.
early elute: 120.5 mg off white solid
later elute: 81.5 mg white solid Early Elute NMR Characterizing Data for 100% Pure Compound $^1$H NMR ($CDCl_3$, 500 MHz): 8.2–7.3(m, 15 H), 7.04(d, 1H), 6.39(S, 1H), 6.18(t, 1H), 5.78(d, 1H), 5.68(d, 1H), 4.92(d, 1H), 4.78 (d, 1H), 4.56(d, 1H), 4.42(d, 1H), 4.30(d, 1H), 4.23–4.17(m, 2H), 3.83(d, 1H), 3.61(d, 1H), 2.91(m, 1H), 2.48(s, 3H), 2.37(s, 3H), 2.31(d, 1H), 2.21(s, 3H), 1.97(m, 1H), 1.84(s, 3H), 1.78(s, 1H), 1.76(s, 3H), 1.21(s, 3H) and 1.19(s, 3H)

Later Elute NMR Characterizing Data for 100% Pure Compound $^1$H NMR ($CDCl_3$, 500 MHz): 8.2–7.3(m, 15 H), 7.08(d, 1H), 6.38(S, 1H), 6.19(t, 1H), 5.78(d, 1H), 5.66(d, 1H), 4.91(d, 1H), 4.80 (d, 1H), 4.62(d, 1H), 4.39(d, 1H), 4.30(d, 1H), 4.16(m, 2H), 3.82(d, 1H), 3.68(d, 1H), 2.78(m, 1H), 2.49(s, 3H), 2.38(s, 3H), 2.31(d, 1H), 2.21(s, 3H), 1.85(m, 1H), 1.83(s, 3H), 1.78(s, 1H), 1.73(s, 3H), 1.21(s, 3H) and1.18(s, 3H)

The compounds of this invention exhibit antitumor activities in in vivo and/or in vitro models. For example, the following test describes the in vitro test used to evaluate some representative compounds of this invention.

Cytoxicity

The taxane derivatives possessed cytoxicity in vitro against human colon carcinoma cells HCT-116. Cytotoxicity was assessed in HCT116 human colon carcinoma cells by XTT (2,3-bis(2-methoxy-4-nitro-5-sulfophenyl)-5-[(phenylamino)carbonyl]-2H-tetrazolium hydroxide assay (1). Cells were plated at 4000 cells/well in 96 well microtiter plates and 24 hrs later drugs were added and serial diluted. The cells were incubated at 37° C. for 72 hrs at which time the tetrazolium dye, XTT, containing phenazine methosulfate was added. A dehydrogenase enzyme in live cells reduces the XTT to a form that absorbs light at 450 nm which can be quantitated spectrophotometrically. The greater the absorbance the greater the number of live cells. The results are expressed as an IC50 which is the drug concentration required to inhibit cell proliferation (i.e. absorbance at 450 nm) to 50% of that of untreated control cells.

The $IC_{50}$ values for compounds evaluated in this assay are contained in Table I.

TABLE I

| Compound | Cytotoxicity Assay $IC_{50}$ (nM) against HCT 116 Human colon tumor cell line |
|---|---|
| 2 & 3 (Example 1) | 13 |
| 4 (Example 2) | 2.8 |
| paclitaxel | 4.9–5.9 |

Mice M109 Model (In-Vivo Activity)

Balb/c×DBA 2 $F_1$ ($CDF_1$) hybrid mice were implanted subcutaneously (sc) with 0.1 mL of a 2% (w/v) brei of M109 lung carcinoma (as described by William Rose in *Evaluation of Madison 109 Lung Carcinoma as a Model for Screening Antitumor Drugs, Cancer Treatment Reports*, 65, No. 3–4 (1981)).

The test compounds and reference drug, paclitaxel, were administered intravenously to groups of mice; each group received a compound at a different dose level, and three or four different dose levels were evaluated per compound. Mice were treated with compounds intravenously, once daily, on days 4, 5, 6, 7, and 8 post-tumor implant. Mice were followed daily for survival until their death or approximately 60–90 days post-tumor implant whichever occurred first. One group of mice per experiment remained untreated and served as the primary control group; a secondary control group was typically included and received 1/10th the tumor inocula of all the other groups of mice (i.e., 0.1 ml of a 0.2% (w/v) brei of M109 lung carcinoma). Tumors were also measured once or, more often, twice weekly to estimate the tumor weight according to the published procedure (ibid).

Median survival times of compound-treated (T) mice were compared to the median survival time of the control (C) mice. The ratio of the two values for each compound-treated group of mice was multiplied by 100 and expressed as a percentage (i.e. % T/C in the following Table II for representative compounds. Additionally, the difference between the median time for treated groups and that for the control group to grow tumor to 1 gm, expressed as T-C values in days, is also shown in the following table. The greater the T-C value, the greater the delay in primary tumor growth. Compounds showing % T/C≧125% and/or T-C≧4.0 days are considered to be active in the M109 sc model provided the aforementioned secondary control group does not differ by more than 4 days from the primary control group with regard to the median time to grow 1 gm tumors. When the difference in the time to grow 1 gm tumors in both primary and secondary control groups is greater than 4 days, that difference becomes the criterion for activity.

Advanced Distal Site Antitumor IV Testing of
Paclitaxel Derivatives

TABLE II

| Compound | Maximum Effect | | Opt. dose |
|---|---|---|---|
| | % T/C | T-C days | (mg/kg/inj) |
| 2 & 3 | 129 | 10.0 | 25 |
| (first 90:8 sulfoxide mixture from example 3) | 141 | 9.0 | 15 |

Thus, another aspect of the instant invention concerns a method for inhibiting human and/or other mammalian tumors which comprises administering to a tumor bearing host an antitumor effective amount of a compound of formula I.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mg/m$^2$ over 1 to 100 hours. Via the oral route, the dosage may be in the range of 5–1000mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I, or a pharmaceutically acceptable salt thereof wherein: R is aryl, substituted aryl, $C_{1-6}$ alkyl, $C_{2-6}$ alkenyl, $C_{3-6}$ cycloalkyl, or heteroaryl;
$R^A$ is hydrogen;
$R^B$ is independently —NHC(O)-aryl, —NHC(O)-substituted aryl, —NHC(O)-heteroaryl, —NHC(O)OCH$_2$Ph, or —NHC(O)O—($C_{1-6}$ alkyl);
$R^C$ is hydrogen;
$R^D$ is hydroxy;
$R^2$ is phenyl or substituted phenyl;
$R^4$ is methyl, ethyl, propyl, cyclopropyl or —O—($C_1$–$C_3$ alkyl);
L is O;
$R^6$ and $R^{6'}$ are hydrogen;
One of $R^{7'}$ and $R^7$ is hydrogen and the other is —OCH$_2$S(O)$_n$CH$_3$;
n=1 or 2;
$R^9$ and $R^{9'}$ are independently hydrogen or hydroxy or $R^9$ and $R^{9'}$ together form an oxo (keto) group;
$R^{10}$ is hydrogen, hydroxy or —OC(O)—($C_1$–$C_6$ alkyl);
$R^{10'}$ hydrogen;
$R^{14}$ is hydrogen or hydroxy; and
$R^{19}$ is methyl.

2. A compound of claim 1 or a pharmaceutically acceptable salt thereof

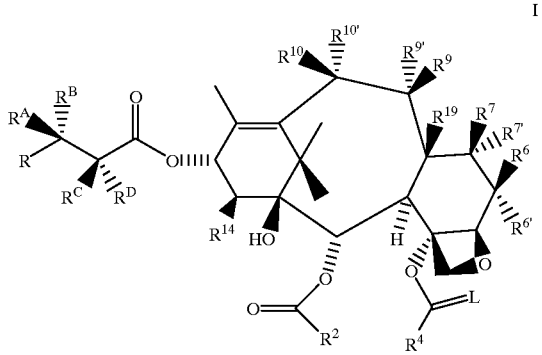

wherein R is phenyl, p-hydroxyphenyl, p-fluorophenyl, p-chlorophenyl, p-Tolyl, isopropyl, isopropenyl, isobutenyl, isobutyl, cyclopropyl, furyl, or thienyl;
$R^A$ is hydrogen;
$R^B$ is independently —NHC(O)Ph, or —NHC(O)O—(C$_{1-6}$ alkyl);
$R^C$ is hydrogen;
$R^D$ is hydroxy;
$R^2$ is phenyl;
$R^4$ is methyl;
L is O;
$R^6$ and $R^{6'}$ are hydrogen;
$R^{7'}$ is hydrogen;
$R^7$ is —OCH$_2$S(O)$_n$CH$_3$;
n=1 or 2;
$R^9$ and $R^{9'}$ together form an oxo (keto) group;
$R^{10}$ is hydroxy or —OC(O)CH$_3$;
$R^{10'}$ is hydrogen;
$R^{14}$ is hydrogen; and
$R^{19}$ is methyl.

3. Compounds of claim 1 or pharmaceutically acceptable salts thereof

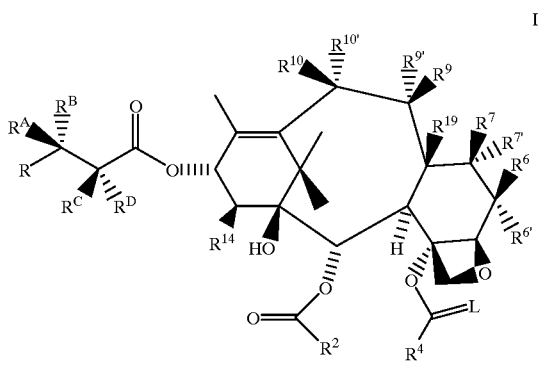

wherein R is phenyl;
$R^A$ is hydrogen;
$R^B$ is —NHC(O)Ph;
$R^C$ is hydrogen;
$R^D$ is hydroxy;
$R^2$ is phenyl;
$R^4$ is methyl;
L is O;
$R^{6'}$ and $R^6$ are each hydrogen;
$R^{7'}$ is hydrogen;
$R^7$ is —OCH$_2$S(O)$_n$CH$_3$;
n=1 or 2;
$R^9$ and $R^{9'}$ together form an oxo (keto) group;
$R^{10}$ is —OC(O)CH$_3$;
$R^{10'}$ is hydrogen;

$R^{14}$ is hydrogen; and
$R^{19}$ is methyl.

4. A compound of claim 3 wherein $R^7$ is —OCH$_2$S(O)CH$_3$.

5. A compound of claim 3, wherein $R^7$ is —OCH$_2$S(O)CH$_3$ as a single diastereomer with the formula shown below:

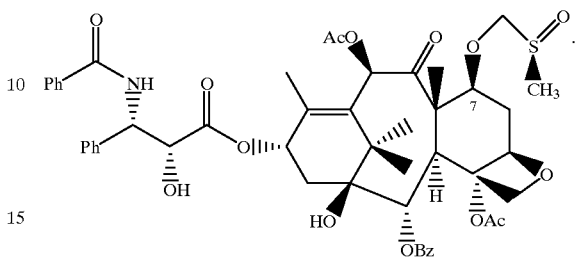

6. A compound of claim 3, wherein $R^7$ is —OCH$_2$S(O)CH$_3$ as a single diastereomer with the formula shown below:

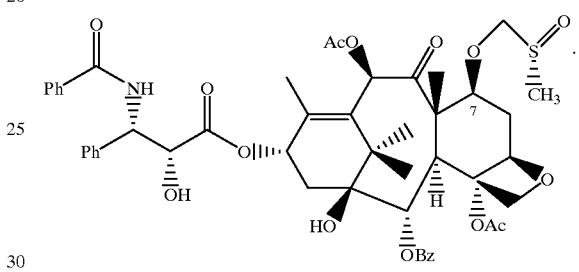

7. A compound of claim 3, wherein $R^7$ is —OCH$_2$S(O)$_2$CH$_3$ with the formula shown below:

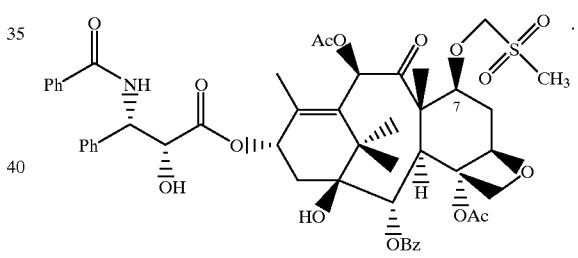

8. A compound of claim 2, wherein
R is phenyl;
$R^B$ is —NHC(O)O—tBu;
$R^7$ is —OCH$_2$S(O)$_2$CH$_3$; and
$R^{10}$ is —OC(O)CH$_3$
with the formula shown below:

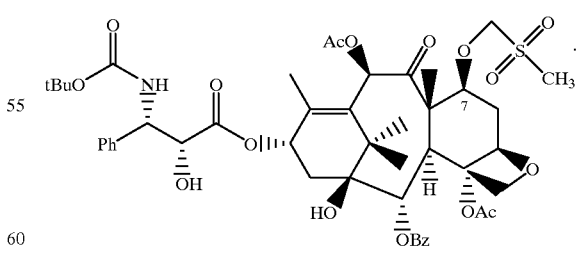

9. A compound of claim 2, wherein
R is phenyl;
$R^B$ is —NHC(O)O—tBu;
$R^7$ is —OCH$_2$S(O)CH$_3$; and
$R^{10}$ is —OC(O)CH$_3$ with the formula shown below:
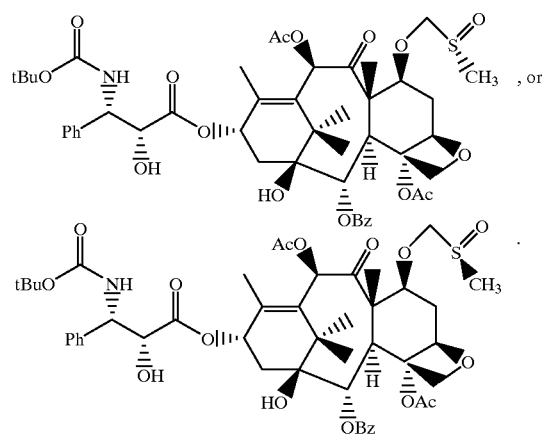
10. A pharmaceutical formulation which copmrises an antitumor effective amount of a compound of formula I as claimed in any one of claims 1–9.
11. A method for inhibiting tumor growth in a mammalian host which comprises administering to said mammal a tumor-growth inhibiting amount of a compound of formula I as claimed in any one of claims 1–9.
* * * * *

UNITED STATES PATENT AND TRADEMARK OFFICE
CERTIFICATE OF CORRECTION

PATENT NO: 5,902,822

DATED: May 11, 1999

INVENTOR(S): Jerzy Golik, et al

It is certified that error appears in the above-identified patent and that said Letters Patent is hereby corrected as shown below:

In claim 1, line 62, insert the word "is" after the term "$R^{10'}$" and before "hydrogen;"

In claim 10, line 1, change the term "copmrises" to read "comprises."

Signed and Sealed this

Eighth Day of February, 2000

*Attest:*

Q. TODD DICKINSON

*Attesting Officer*   *Commissioner of Patents and Trademarks*